United States Patent

Taguchi

(10) Patent No.: US 10,420,855 B2
(45) Date of Patent: Sep. 24, 2019

(54) SURGICAL SEALANT

(71) Applicant: NATIONAL INSTITUTE FOR MATERIALS SCIENCE, Ibaraki (JP)

(72) Inventor: Tetsushi Taguchi, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 0 days.

(21) Appl. No.: 15/544,610

(22) PCT Filed: Jan. 19, 2016

(86) PCT No.: PCT/JP2016/051463
§ 371 (c)(1),
(2) Date: Jul. 19, 2017

(87) PCT Pub. No.: WO2016/117569
PCT Pub. Date: Jul. 28, 2016

(65) Prior Publication Data
US 2018/0272028 A1    Sep. 27, 2018

(30) Foreign Application Priority Data

Jan. 20, 2015    (JP) ................................. 2015-008556

(51) Int. Cl.
*A61K 47/42*    (2017.01)
*A61L 24/10*    (2006.01)
(Continued)

(52) U.S. Cl.
CPC ............ *A61L 24/043* (2013.01); *A61L 24/00* (2013.01); *A61L 24/104* (2013.01); *A61L 26/0038* (2013.01); *A61K 47/42* (2013.01)

(58) Field of Classification Search
CPC .... A61K 38/1706; A61K 38/39; A61K 47/42; A61L 24/104; A61L 24/043; A61L 26/0038; C07K 14/461; C07K 14/78
See application file for complete search history.

(56) References Cited

U.S. PATENT DOCUMENTS 7,273,896 B2 * 9/2007 Daniloff .................. A61L 27/50
424/426
2005/0069589 A1 * 3/2005 Lowinger ............. A61L 24/102
424/488
(Continued)

FOREIGN PATENT DOCUMENTS

EP    2 626 086    8/2013
JP    9-103479    4/1997
(Continued)

OTHER PUBLICATIONS

Vyas et al. Comparison of hemostatic agents used in vascular surgery. Expert Opinion on Biological Therapy. 2013, vol. 13, No. 12, pp. 1663-1672. (Year: 2013).*
(Continued)

*Primary Examiner* — Jeffrey E. Russell
(74) *Attorney, Agent, or Firm* — Wenderoth, Lind & Ponack, L.L.P.

(57) ABSTRACT

A surgical sealant comprising a first agent containing a hydrophobically-modified gelatin derived from a cold-water fish, and a second agent containing a water-soluble molecule for crosslinking, wherein the water-soluble molecule for crosslinking is at least one kind selected from the group consisting of poly acids and acid anhydrides having two or more active ester groups, and aldehyde compounds having two or more aldehyde groups, the hydrophobically-modified gelatin derived from a cold-water fish is a gelatin in which at least a part of amino groups of side chains of a gelatin derived from a cold-water fish has been substituted by hydrophobic groups, and the hydrophobic groups are linear chain aliphatic groups each having 8 to 18 carbon atoms, with a substitution rate (number of moles of hydrophobic groups/(total number of moles of hydrophobic groups and reactive amino groups in gelatin)×100) of 3 to 20 mol %.

6 Claims, 11 Drawing Sheets

(51) Int. Cl.
*A61L 26/00* (2006.01)
*A61L 24/04* (2006.01)
*A61L 24/00* (2006.01)

(56) References Cited

U.S. PATENT DOCUMENTS

| | | | | |
|---|---|---|---|---|
| 2008/0253987 | A1* | 10/2008 | Rehor | A61L 24/046 424/78.37 |
| 2011/0066182 | A1* | 3/2011 | Falus | A61L 24/0031 606/214 |
| 2013/0220174 | A1* | 8/2013 | Taguchi | A61L 24/104 106/155.21 |
| 2014/0154204 | A1* | 6/2014 | Clower | A61K 31/80 424/78.37 |
| 2015/0359924 | A1 | 12/2015 | Taguchi | |

FOREIGN PATENT DOCUMENTS

| | | | |
|---|---|---|---|
| JP | 2008-284256 | 11/2008 | |
| JP | 2014-100420 | 6/2014 | |
| WO | 2004/087227 | 10/2004 | |
| WO | WO-2014112208 A1 * | 7/2014 | ........... A61L 24/104 |
| WO | 2015/076252 | 5/2015 | |

OTHER PUBLICATIONS

Ryo Mizuta et al., "Sealing effect of hydrophobically modified, cod-derived gelatin for wet tissue", Polymer Reprints, Japan, vol. 63, No. 1 (2014), pp. 3627-3628, with English translation.
Ryo Mizuta et al., "Development of Hydrophobically-modified, Pollock-derived Gelatin-based Biocompatible Sealants", Polymer Preprints, Japan, vol. 64, No. 2, Aug. 25, 2015, with English translation.
Tetsushi Taguchi et al., "Development trend of medical adhesive with high biocompatibility", Engineering Materials, Jun. 1, 2015, vol. 63, No. 6, pp. 44-50, with English translation.
International Search Report dated Mar. 8, 2016 in corresponding International (PCT) Application No. PCT/JP2016/051463.
Written Opinion of the International Searching Authority dated Mar. 8, 2016 in corresponding International (PCT) Application No. PCT/JP2016/051463.
Tetsushi Taguchi et al., "Biodegradable Adhesives Composed of Human Serum Albumin and Organic Acid-based Crosslinkers with Active Ester Groups", Journal of Bioactive and Compatible Polymers, vol. 24, 2009, pp. 546-559.
Office Action dated Mar. 27, 2018 in Japanese Application No. 2016-570661, with English translation.
Extended European Search Report dated Oct. 12, 2018 in European Application No. 16740176.9.

* cited by examiner

FIG.1
4S-PEG
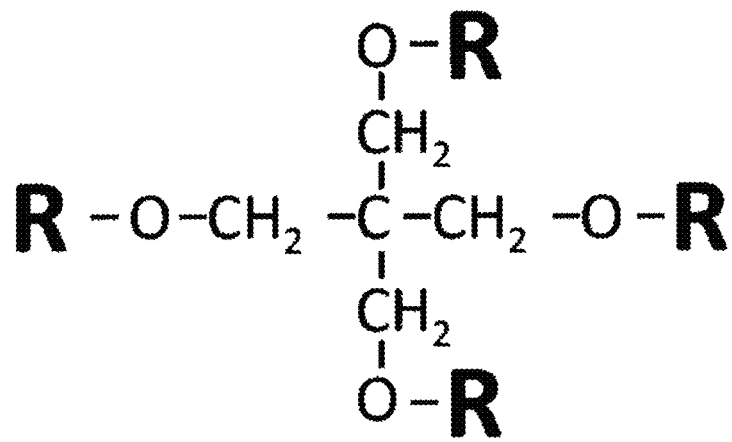
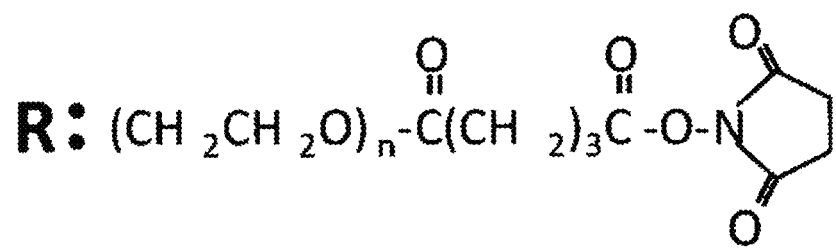

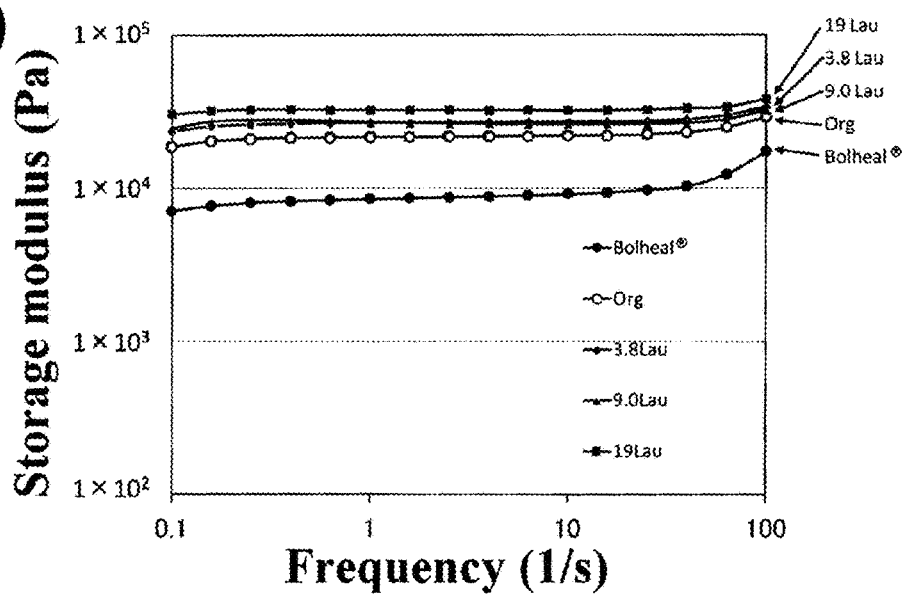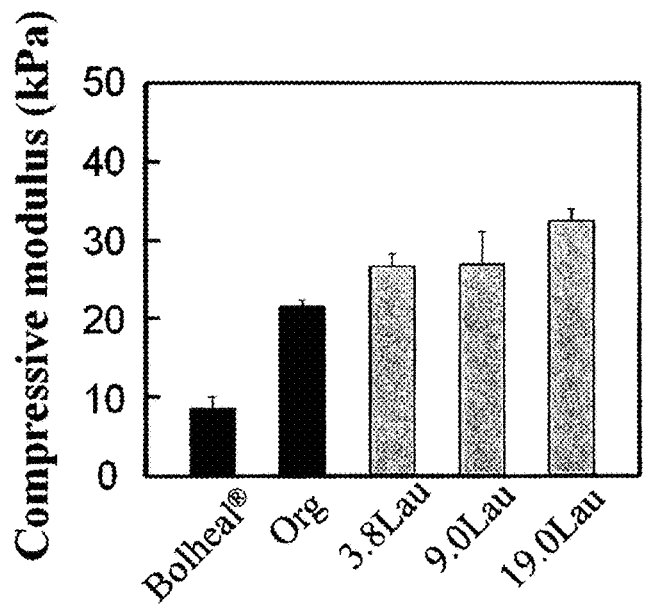

SURGICAL SEALANT

TECHNICAL FIELD

The present invention relates to a surgical sealant.

BACKGROUND ART

A surgical sealant (hereinafter referred to as "sealant") is a material that is applied after suturation of an affected part in a biological tissue (hereinafter referred to as "tissue") such as blood vessel and skin and forms a membrane to thereby prevent emigration of blood and body fluid, oozing, leakage of gas, and the like. The scope of surgical applications includes respiratory surgery, digestive system surgery, cardiovascular surgery, oral cavity surgery and the like. For a surgical sealant, (1) excellent application property, (2) high strength of a gel membrane formed from the sealant, and (3) a short gelation time, are required. Furthermore, it is preferable that (4) the gel membrane has high interfacial adhesion strength against a tissue, and (5) the gel membrane provides small change in water content and is excellent in flexibility.

Currently, sealants that are mainly used are fibrin-based surgical sealants, and Bolheal (trade name, manufactured by Kaketsuken) is exemplified as a product. This surgical sealant is constituted by a component derived from a biological body, and thus has high biocompatibility, but has a problem that it has low adhesion strength.

It has been clarified in recent years that a surgical sealant including human serum albumin (Human Serum Albumin: hereinafter HSA) and a crosslinker has high adhesion strength (Non-patent Literature 1). HSA is a blood serum protein made from a blood product, and is a globular, negatively-charged acidic protein having a molecular weight of 69,000 and a diameter of about 10 nm. Furthermore, as the crosslinker, tartaric acid (Disuccinimidyl Tartarate: hereinafter DST) is used. However, when a blood product is used, the surgical sealant is classified into a medicament, and thus requires much labor in view of acceptation and approval. Furthermore, in the case when the surgical sealant is deemed as a medicament, the history of use thereof should be continuously kept for 20 years after the approval, and thus there is a problem that much labor is required.

Therefore, use of a gelatin, which is a non-blood product, instead of HSA, has been considered. For example, Patent Literature 1 discloses a medical material prepared by crosslinking a gelatin with poly(L-glutamic acid) derivative with succinimdyl groups. Furthermore, Patent Literature 2 relates to a tissue adhesion film, and discloses a tissue adhesion film made from a gelatin or a collagen. However, these materials have a problem that their sealing strength, for which both membrane strength and interfacial adhesion strength are required, are insufficient. Furthermore, Patent Literature 3 relates to a tissue adhesion constitution, and discloses a tissue adhesion constitution in which a particulate synthesis and/or crosslinkable material and a particulate material are mixed. However, this tissue adhesion constitution also has a problem that it has insufficient sealing strength.

In order to solve the above-mentioned problems, the present inventors have synthesized a gelatin having hydrophobic groups at the side chains by using a method for derivatizing a gelatin (Non-patent Literature 1), and suggested a tissue adhesive including said gelatin and a crosslinker (Patent Literature 4).

CITATION LIST

Patent Literature

Patent Literature 1: JP 09-103479 A
Patent Literature 2: JP 2008-284256 A
Patent Literature 3: JP 2006-523113 W
Patent Literature 4: WO 2014/112208 A

Non-Patent Literature

Non-patent Literature 1: J. Bioact. Compact. Polym., 24, 546-559 (2009)

SUMMARY OF INVENTION

Technical Problem

The above-mentioned tissue adhesive shows an excellent adhesion strength on a tissue. However, as mentioned above, a sealant is required to have not only adhesion strength but also the strength of a membrane itself for withstanding a pressure from blood or body fluid (hereinafter referred to as "membrane strength"). Therefore, the present invention aims at further improving the above-mentioned adhesive in view of membrane strength to thereby provide an excellent sealant.

Solution to Problem

The inventors have done various considerations, and found that excellent membrane strength, and thus excellent sealing strength can be achieved in the case when hydrophobic groups are aliphatic groups having a predetermined carbon number, and completed the present invention.

Specifically, the present invention has the following constitutions.

(1) A surgical sealant comprising:
a first agent containing a hydrophobically-modified gelatin derived from a cold-water fish, and
a second agent containing a water-soluble molecule for crosslinking,
wherein the water-soluble molecule for crosslinking is at least one kind selected from the group consisting of poly acids and acid anhydrides having two or more active ester groups, and aldehyde compounds having two or more aldehyde groups,
the hydrophobically-modified gelatin derived from a cold-water fish is a gelatin in which at least a part of amino groups of side chains of a gelatin derived from a cold-water fish has been substituted by hydrophobic groups, and
the hydrophobic groups are linear chain aliphatic groups each having 8 to 18 carbon atoms, with a substitution rate (number of moles of hydrophobic groups/(total number of moles of hydrophobic groups and reactive amino groups in gelatin)×100) of 3 to 20 mol %.

(2) The surgical sealant according to (1), wherein the hydrophobically-modified gelatin derived from a cold-water fish has a molecular weight of 10,000 or more and 150,000 or less.

(3) The surgical sealant according to (1), wherein the gelatin derived from a cold-water fish is one kind or a combination of two or more kinds from gelatins derived from red snapper, tilapia, cod and salmon, or genetically-engineered cold-water fishes thereof.

(4) The surgical sealant according to (1), wherein the gelatin derived from a cold-water fish contains 190 or less imino acids per 1,000 constitutional amino acids.

(5) The surgical sealant according to (1), wherein the hydrophobic groups are linked to a part of the amino groups of Lys that is one of the constitutional amino acids of the gelatin derived from a cold-water fish.

(6) The surgical sealant according to (1), wherein the water-soluble molecule for crosslinking is one kind, or a combination of two or more kinds selected from the group consisting of polyethylene glycol disuccinimidyl succinate, pentaerythritol-poly(ethylene glycol) ether tetrasuccinimidyl glutarate and poly-L-glutamic acid succinimide.

(7) The surgical sealant according to (1), wherein the first agent is used in the form of an aqueous solution having a pH of 8 to 11, the second agent is used in the form of an aqueous solution having a pH of 3 to 8, and the first and second agents are used by mixing so that a mixed solution thereof has a pH of 8 to 9.

Advantageous Effect of Invention

The hydrophobically-modified gelatin derived from a cold-water fish (hereinafter sometimes referred to as "hydrophobically-modified gelatin") for the surgical sealant of the present invention has linear chain aliphatic groups each having 8 to 18 carbon atoms, and thus shows a high membrane strength. In the sealant described in Patent Literature 4, in the case when the gelatin has these groups, an equivalent adhesion strength cannot be shown unless the substitution rate is considerably increased, since the adhesion strength is weaker than those in the cases when the gelatin has groups having lesser carbons and alicyclic groups. However, it was surprisingly found that, in view of membrane strength, which can be evaluated by compression strength, the surgical sealant having these groups have significantly higher membrane strength, which is more than make up for low adhesion strength even at a low substitution rate, and consequently shows high sealing strength. Said surgical sealant is very useful for a surgical operation for which prevention of leaking of blood and the like is important such as an anastomotic operation of blood vessels.

BRIEF DESCRIPTION OF DRAWINGS

FIG. 1 is a drawing showing an example of the water-soluble molecule for crosslinking in a second agent for the surgical sealant of the present invention.

FIG. 7(a) shows a graph showing the angle frequency wave number dependency of the storage moduluses of 3.8Lau-cGltn (Example 2), 9.0Lau-cGltn (Example 3) and 19.0Lau-cGltn (Example 4), and FIG. 7(b) shows a bar graph showing the compressive moduluses.

DESCRIPTION OF EMBODIMENTS

<Water-Soluble Molecule for Crosslinking>

Figure 2:
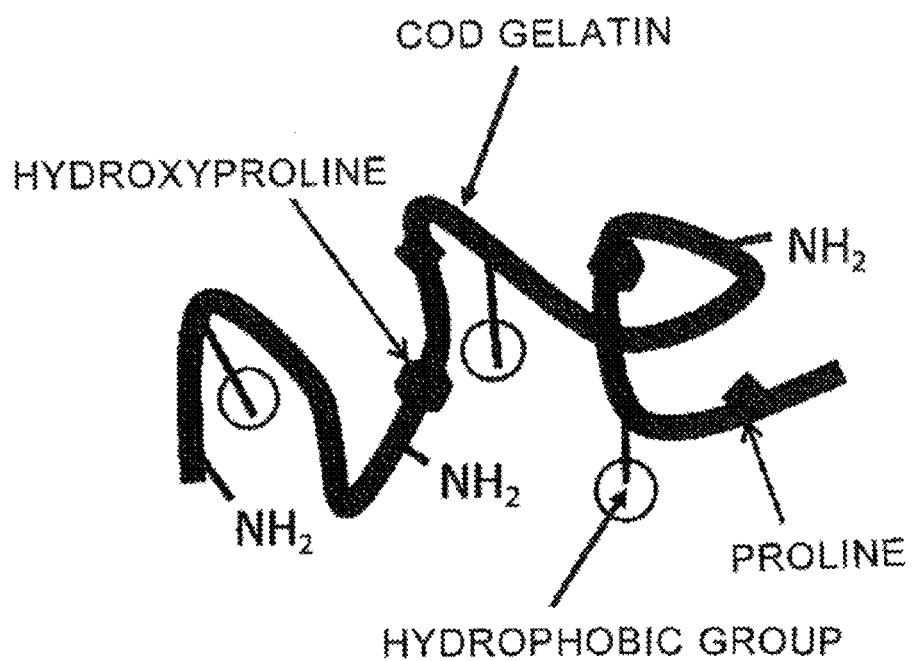
FIG. 2 is an explanation drawing showing an example of the hydrophobically-modified gelatin derived from a cold-water fish in a first agent for the surgical sealant of the present invention.

FIG. 1 is a drawing showing the structure of pentaerythritol-poly(ethylene glycol) ether tetrasuccinimidyl glutarate (abbreviation: 4S-PEG) as an example of the water-soluble molecule for crosslinking in the second agent of in the surgical sealant of the present invention. In this drawing, n is a number at which the molecular weight (Mn) becomes about 8,000 to 12,000. 4S-PEG has active ester groups that react with a hydrophobically-modified gelatin at the terminals of the branched chains containing PEG residues. 4S-PEG has high biological safeness, and easily dissolves in water.

The water-soluble molecule for crosslinking is at least one kind selected from the group consisting of poly acids and acid anhydrides having two or more active ester groups, and aldehyde compounds having two or more aldehyde groups. These groups react with the active esters and the reactive amino groups in the hydrophobically-modified gelatin to form a crosslinked structure.

The above-mentioned active ester groups are preferably of one kind or a combination of two or more kinds of N-hydroxysuccinimidyl, or ester groups activated with N-hydroxysulfosuccinimidyl groups. Succinimide is a derivative of succinic acid, which is present in a metabolic pathway in a biological body, and has a good track record of use in surgical sealants that were approved by the U.S. Food and Drug Administration.

As the polybasic acid, tartaric acid, citric acid, malic acid, glutaric acid, glutamic acid, asparagine acid, oxaloacetic acid, cis-aconitic acid, 2-ketoglutalic acid, polytartric acid, polycitric acid, polymalic acid, polyglutamic acid, polyaspartic acid and the like are exemplified, and for example, disuccinimidyl glutarate (DSG), disuccinimidyl suberate (DSS), disuccinimidyl tartarate (DST), poly-L-glutamic acid succinimidyl and the like can be used.

As preferable examples of the polybasic acid having two or more active ester groups, besides the above-mentioned 4S-PEG, one kind or a combination of two or more kinds of a polyethylene glycol disuccinimidyl succinate represented by the following formula (PEG-(SS) 2):

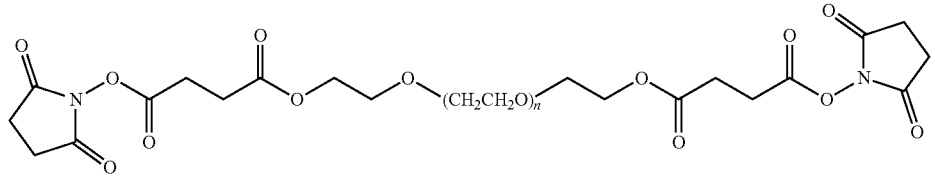

[Chemical Formula 1]

(n is a number at which Mn is about 20,000) poly-L-glutamic acid succinimide can be used.

As the aldehyde compound, aldehyde group-introduced polysaccharides in which two or more aldehyde group have been introduced in one molecule such as aldehyde group-introduced starch, aldehyde group-introduced dextran and aldehyde group-introduced hyaluronic acid are exemplified. As the acid anhydride, glutalic anhydride, maleic anhydride and succinic anhydride are exemplified, and as the diisothiocyanate, hexamethylene diisothiocyanate and the like are exemplified.

Said crosslinker is used in an amount such that the active groups in said crosslinker, such as ester groups activated with N-hydroxysuccinimidyl groups becomes 0.2 to 3 equivalent amount, preferably 0.3 to 2 equivalent amount, more preferably 0.4 to 1.5 equivalent amount, the most preferably 0.5 to 1.2 equivalent amount with respect to one equivalent amount of the reactive amino groups in the hydrophobically-modified gelatin. A mixture of two or more kinds of crosslinkers may also be used, and in such case, the amount is set to an amount such that the total equivalent amount of those crosslinkers is within the above-mentioned range.

It is preferable that the second agent is used in the form of an aqueous solution having a pH of 3 to 8, and the pH is more preferably 4 to 6. As the aqueous solvent for setting to said pH, ultrapure water, saline, various buffer solutions, phosphate buffer saline (hereinafter referred to as "PBS") or mixtures thereof can be used.

<Hydrophobically-Modified Gelatin Derived from Cold-Water Fish>

FIG. 2 is an explanation drawing showing an example of the hydrophobically-modified gelatin derived from a cold-water fish contained in the first agent for the surgical sealant of the present invention. Said hydrophobically-modified gelatin is a gelatin formed by substituting a part of the amino groups of the side chains of a gelatin derived from a cold-water fish with hydrophobic groups. A part of the amino groups of Lys, which is one of the amino acids that constitute the gelatin derived from a cold-water fish, is substituted with hydrophobic groups. Lys is one of α-amino acids that constitute proteins, and has an ε-amino group as a side chain.

The hydrophobically-modified gelatin derived from a cold-water fish has a molecular weight (Mw) of preferably 10,000 to 150,000, more preferably 10,000 to 120,000, the most preferably 10,000 to 100,000. A membrane obtained from a gelatin having a molecular weight within the above-mentioned range and a crosslinker has high strength and fine handling property. The hydrophobically-modified gelatin derived from a cold-water fish has high solubility in aqueous solvents, is not gelled, and can be stored in a liquid form.

The gelatin derived from a cold-water fish is not limited to cod gelatin, and may also be red snapper gelatin, tilapia gelatin, salmon gelatin or the like, or a genetically-engineered gelatin thereof. Natural cod gelatin is preferable.

The gelatin derived from a cold-water fish is a polymer in which two or more amino acids are ligated in a linear manner, and has 190 or less molecules of imino acid, i.e., 80 or less molecules of hydroxyproline and 110 or less molecules of proline per 1,000 molecules of the constitutional amino acids. It is considered that the fluidity of the gelatin derived from a cold-water fish at an ordinary temperature is attributed to the number of hydroxyproline is 80 or less or the number of proline is 110 or less. It is considered that, when either of the conditions is satisfied, the denaturation temperature becomes approximately room temperature or less, and fluidity at an ordinary temperature is caused.

Red snapper gelatin has a hydroxyproline number of 73, a proline number of 108 and a denaturation temperature of 302.5 K. Tilapia gelatin has a hydroxyproline number of 82, a proline number of 110 and a denaturation temperature of 309 K. With respect to these gelatins, porcine gelatin has a hydroxyproline number of 95, a proline number of 121, and a denaturation temperature of 316 K.

The gelatin derived from a cold-water fish has a similar amino acid sequence to that of a gelatin derived from an animal, is easily decomposed by an enzyme, and has high biocompatibility.

It is preferable that the first agent is used in the form of a solution having a pH of 8 to 11, and a pH of 9 to 10 is more preferable. As an aqueous solvent for setting to said pH, a borate buffer solution can be used. The concentration of the hydrophobized cold-water fish gelatin in the first agent aqueous solution is in the range of 10 to 40 w/v %, preferably 15 to 30 w/v %.

<Hydrophobic Group>

The hydrophobic group has a substitution rate (mol %), i.e., (number of moles of hydrophobic groups/(total number of moles of hydrophobic groups and reactive amino groups in gelatin)×100 of 3 to 20 mol %, preferably 3 to 12 mol %, more preferably 5 to 10 mol %. When the substitution rate is less than the above-mentioned lower limit value, the compressive modulus tends to be low, whereas when the substitution rate goes beyond the above-mentioned upper limit value, the first agent aqueous solution may become cloudy, or may have a high viscosity.

The hydrophobic group is a linear chain aliphatic group having 8 to 18 carbon atoms, preferably 8 to 14 carbon atoms. Said substituent is linked to the gelatin via an amide group or the like. Examples of the linear chain aliphatic group include an octanoyl group, a nonanoyl group, a decanoyl group, a dodecanoyl group, a tetradecanoyl group, a hexadecanoyl group, a hexadecenoyl group, an octadecanoyl group, an octadecenoyl group and the like.

<Additive>

The above-mentioned first agent aqueous solution and/or second agent aqueous solution may further contain various additives that are conventionally-used in surgical sealants, in an amount at which the purpose of the present invention is not inhibited. Examples of said additives include colorant, pH adjusting agents, viscosity adjusting agents and the like. Preferably, a colorant is added to the first agent or the second agent, more preferably, Brilliant Blue is added to the first agent at 0.001 to 0.1 wt % of the weight of the first agent, whereby a portion to be operated is clarified.

<Method for Producing Surgical Sealant>

In the surgical sealant of the present invention, the first agent and the second agent are individually prepared, and the two agents are mixed during or immediately before application.

[Method for Preparing First Agent]

(1) Preparation of Starting Gelatin Solution

A gelatin as a starting material is dissolved in an organic solvent such as dimethylsulfoxide at an amount at which the gelatin becomes 5 to 50 wt/v %.

(2) Hydrophobic Modification

A derivatized agent having a hydrophobic group is added to the gelatin solution obtained in Step (1), and a reaction is conducted by stirring for a predetermined time. As said derivatized agent, an organic acid or acid chloride having the above-mentioned hydrophobic group can be used. The organic acid or acid chloride in an amount that gives an intended substitution rate is added to an organic solvent solution of the gelatin, and the mixture is heated under an inert gas atmosphere at 60 to 100° C., and stirred overnight.

(3) Purification

A poor solvent such as cold ethanol in a large excess amount is added to the reaction solution obtained in Step (2) to thereby precipitate a gelatin derivative. Said precipitate is filtered off, and washed with ethanol, ethyl acetate or the like to give a final product.

(4) Preparation of First Agent Aqueous Solution

The gelatin derivative obtained in Step (3) is dissolved in a borate buffer solution or the like at 10 to 40 w/v %, preferably 15 to 30 w/v to thereby set the pH to 8 to 11, preferably 9 to 10. Where desired, an underivatized gelatin, and other additives are added.

[Method for Preparing Second Agent]

As the second agent, a commercially available crosslinker may be used, and during the use thereof, the crosslinker is dissolved in an amount within the above-mentioned range in an aqueous solvent such as ultrapure water, PBS or a mixture thereof to thereby set the pH to 3 to 8, preferably 4 to 6.

Preferably, the pHs of the first agent aqueous solution and the second agent aqueous solution are adjusted so that the mixed solution of these aqueous solutions has a pH of 8 to 9. For example, by using a borate buffer solution having a pH of 9 and an ion intensity of 0.05 to 0.1 as the first agent aqueous solution, and using a phosphate buffer having a pH of 4 and an ion intensity of 0.01 to 0.03 as the second agent aqueous solution, the pH can be set to 8 to 9 when the solutions are mixed at equivalent volumes. Alternatively, a borate buffer solution having a pH of 10 and an ion intensity of 0.05 to 0.1 may be used as the first agent aqueous solution and a phosphate buffer solution having a pH of 4 and an ion intensity of 0.01 to 0.07 may be used as the second agent aqueous solution.

<Method for Application to Tissue>

The surgical sealant of the present invention can be applied to ruptured parts of skin, blood vessel, tendon, nerve and tubular tissues such as lymph vessel, and organs such as liver, pancreas and heart. Among these, the surgical sealant is preferably applied to wet tissues such as blood vessel and lung. As the method for the application, the first agent and the second agent may be mixed immediately before applying to a tissue an then applied to the tissue, or may be simultaneously applied by using various two-component type dispensers.

Figure 3:
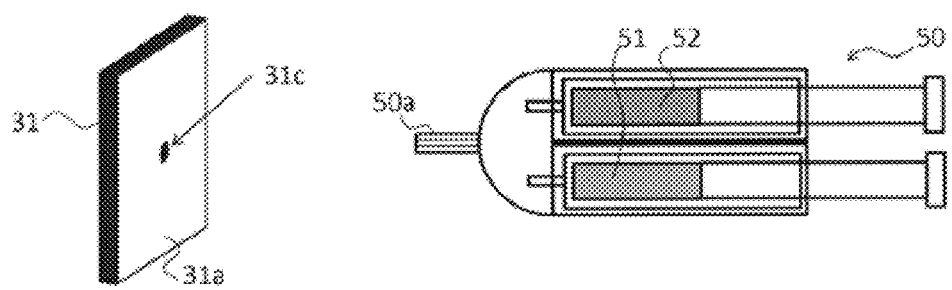
FIGS. 3(a), 3(b) and 3(c) are drawings showing an example of steps for forming a gel membrane using the surgical sealant of the present invention.
Figure 3:
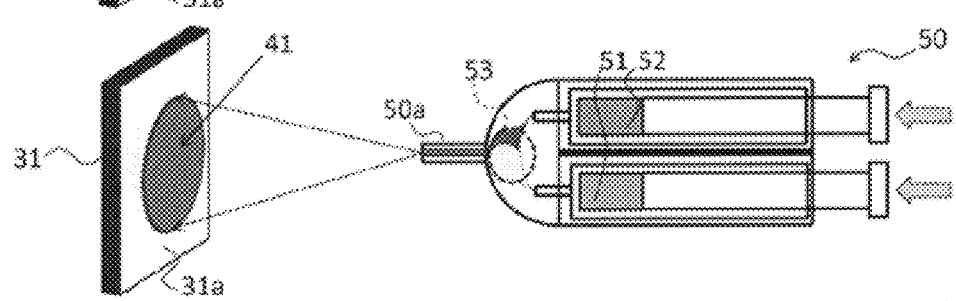
Figure 3:
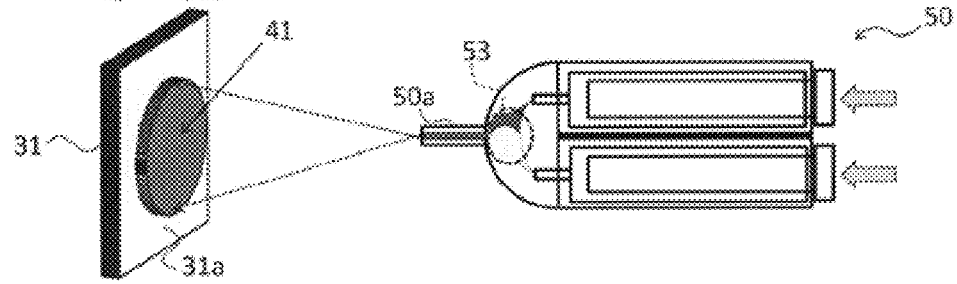

FIGS. 3(a), 3(b) and 3(c) represent a schematic view showing an example of a method for applying the surgical sealant by using a two-component type dispenser. As shown in FIG. 3 (a), to a tissue 31 having an affected part 31c, as shown in FIG. 3 (b), a first agent aqueous solution 51 and a second agent aqueous solution 52 are simultaneously extruded from a double syringe injector 50 in which the two solutions 51 and 52 are stored and mixed in the double syringe injector 50, and a mixed solution 53 is applied onto the tissue 31 from a cylindrical part 50a. As shown in FIG. 3 (c), the two solutions are extruded, and then left for about 10 minutes, whereby a gel membrane 41 having a desired thickness can be formed. The solutions may also be sprayed by an air-assisted spray having a double syringe instead of the dispenser.

EXAMPLES

Reference Signs List

31 . . . tissue, 31a . . . one surface, 31c . . . hole, 41 . . . gel membrane, 50 . . . double syringe injector, 50a . . . cylindrical part, 51 . . . first agent aqueous solution, 52 . . . second agent aqueous solution, 53 . . . mixed solution.

The present invention will be explained with referring to Examples. However, the present invention is not limited to these Examples.

Preparation of Gelatin and Preparation of Surgical Sealant

Reference Example 1

According to the method described in Non-patent Literature 1 using a nucleophilic substitution reaction of an amino group to cholesteryl chloroformate in dimethylsulfoxide, 8.3Chol-cGltn, which is a hydrophobically-modified gelatin derived from a cold-water fish in which 8.3 mol % of the amino groups of the side chains of cod-derived gelatin (Mw=100,000) has been substituted with hydrophobic groups (cholesteryl groups: abbreviated as Chol), was synthesized.

Subsequently, 8.3Chol-cGltn was dissolved at 40 wt % in PBS at pH 8.0 to prepare a first agent aqueous solution. Separately, a water-soluble crosslinker 4S-PEG was dissolved in PBS of pH 8.0 to prepare a second agent aqueous solution. The concentration of 4S-PEG was adjusted so that the equivalent amount ratio of the reactive amino groups of 8.3Chol-Gltn and the active ester groups in 4S-PEG became 1:1 when the first agent aqueous solution and the second agent aqueous solution are mixed at equivalent volumes. This also applies to the following Examples and Comparative Examples.

Example 1

A surgical sealant was prepared in a similar manner to Reference Example 1, except that 9.6Ste-cGltn was synthesized by replacing 9.6 mol % of the amino groups of the side chains of the cod-derived gelatin with hydrophobic groups (stearoyl group: abbreviated as Ste).

Reference Example 2

A surgical sealant was prepared in a similar manner to Reference Example 1, except that 1.9Chol-cGltn was synthesized by replacing 1.9 mol % of the amino groups of the side chains of the cod-derived gelatin with hydrophobic groups (Chol).

Reference Example 3

A surgical sealant was prepared in a similar manner to Reference Example 1, except that 12.2Chol-cGltn was synthesized by replacing 12.2 mol % of the amino groups of the side chains of the cod-derived gelatin with hydrophobic groups (Chol).

Reference Example 4

A surgical sealant was prepared in a similar manner to Reference Example 1, except that 3.2Pro-cGltn was synthesized by replacing 3.2 mol % of the amino groups of the side chains of the cod-derived gelatin with hydrophobic groups (propanoyl groups: abbreviated as Pro).

Reference Example 5

A surgical sealant was prepared in a similar manner to Reference Example 1, except that 6.4Pro-cGltn was synthesized by replacing 6.4 mol % of the amino groups of the side chains of the cod-derived gelatin with hydrophobic groups (Pro).

Reference Example 6

A surgical sealant was prepared in a similar manner to Reference Example 1, except that 13.7Pro-cGltn was synthesized by replacing 13.7 mol % of the amino groups of the side chains of the cod-derived gelatin with hydrophobic groups (Pro).

Reference Example 7

A surgical sealant was prepared in a similar manner to Reference Example 1, except that 2.1Hx-cGltn was synthesized by replacing 2.1 mol % of the amino groups of the side chains of the cod-derived gelatin with hydrophobic groups (hexanoyl groups: abbreviated as Hx).

Reference Example 8

A surgical sealant was prepared in a similar manner to Reference Example 1, except that 8.5Hx-cGltn was synthesized by replacing 8.5 mol % of the amino groups of the side chains of the cod-derived gelatin with hydrophobic groups (Hx).

Reference Example 9

A surgical sealant was prepared in a similar manner to Reference Example 1, except that 18.3Hx-cGltn was synthesized by substituting 18.3 mol % of the amino groups of the side chains of the cod-derived gelatin with hydrophobic groups (Hx).

Example 2

A surgical sealant was prepared in a similar manner to Reference Example 1, except that 3.8Lau-cGltn was synthesized by replacing 3.8 mol % of the amino groups of the side chains of the cod-derived gelatin with hydrophobic groups (lauroyl groups: abbreviated as Lau).

Example 3

A surgical sealant was prepared in a similar manner to Reference Example 1, except that 9.0Lau-cGltn was synthesized by replacing 9.0 mol % of the amino groups of the side chains of the cod-derived gelatin with hydrophobic groups (Lau).

Example 4

A surgical sealant was prepared in a similar manner to Reference Example 1, except that 19.0Lau-cGltn was synthesized by replacing 19.0 mol % of the amino groups of the side chains of the cod-derived gelatin with hydrophobic groups (Lau).

Example 5

A surgical sealant was prepared in a similar manner to Reference Example 1, except that 4.0Ste-cGltn was synthesized by replacing 4.0 mol % of the amino groups of the side chains of the cod-derived gelatin with hydrophobic groups (Ste).

Example 6

A surgical sealant was prepared in a similar manner to Reference Example 1, except that 18.7Ste-cGltn was synthesized by substituting 18.7 mol % of the amino groups of the side chains of the cod-derived gelatin with hydrophobic groups (Ste).

Comparative Example 1

A surgical sealant for comparison was prepared in a similar manner to Reference Example 1, except that a raw material cod gelatin (abbreviated as Org-cGltn) was used instead of the hydrophobically-modified gelatin.

Comparative Example 2

Bolheal (trade name) was used as a fibrin sealant.

The contents of the following surgical sealants are shown in Table 1.

TABLE 1

| | Surgical sealant | | | | | |
|---|---|---|---|---|---|---|
| | First agent aqueous solution | | | Second agent aqueous solution | | |
| | Solute | Solvent | Concentration of hydrophobized cod-derived gelatin (wt %) | Solute | Solvent | Concentration of 4S-PEG (mM) |
| Reference Example 1 | 8.3Chol-cGlth | PBS(pH 8) | 40 | 4S-PEG | PBS(pH 8) | 10.09 |
| Example 1 | 9.6Ste-cGltn | PBS(pH 8) | 40 | 4S-PEG | PBS(pH 8) | 9.94 |
| Reference Example 2 | 1.9Chol-cGlth | PBS(pH 8) | 40 | 4S-PEG | PBS(pH 8) | 10.79 |
| Reference Example 3 | 12.2Chol-cGlth | PBS(pH 8) | 40 | 4S-PEG | PBS(pH 8) | 9.66 |
| Reference Example 4 | 3.2Pro-cGlth | PBS(pH 8) | 40 | 4S-PEG | PBS(pH 8) | 10.65 |
| Reference Example 5 | 6.4Pro-cGlth | PBS(pH 8) | 40 | 4S-PEG | PBS(pH 8) | 10.3 |
| Reference Example 6 | 13.7Pro-cGlth | PBS(pH 8) | 40 | 4S-PEG | PBS(pH 8) | 9.49 |
| Reference Example 7 | 2.1Hx-cGlth | PBS(pH 8) | 40 | 4S-PEG | PBS(pH 8) | 10.77 |
| Reference Example 8 | 8.5Hx-cGlth | PBS(pH 8) | 40 | 4S-PEG | PBS(pH 8) | 10.07 |
| Reference Example 9 | 18.3Hx-cGlth | PBS(pH 8) | 40 | 4S-PEG | PBS(pH 8) | 8.99 |
| Example 2 | 3.8Lau-cGlth | PBS(pH 8) | 40 | 4S-PEG | PBS(pH 8) | 10.58 |
| Example 3 | 9.0Lau-cGlth | PBS(pH 8) | 40 | 4S-PEG | PBS(pH 8) | 10.01 |
| Example 4 | 19.0Lau-cGlth | PBS(pH 8) | 40 | 4S-PEG | PBS(pH 8) | 8.91 |
| Example 5 | 4.0Ste-cGlth | PBS(pH 8) | 40 | 4S-PEG | PBS(pH 8) | 10.56 |
| Example 6 | 18.7Ste-cGlth | PBS(pH 8) | 40 | 4S-PEG | PBS(pH 8) | 8.94 |
| Comparative Example 1 | Org-cGltin | PBS(pH 8) | 40 | 4S-PEG | PBS(pH 8) | 11 |
| Comparative Example 2 | Fibrin | PBS(pH 8) | 40 | 4S-PEG | PBS(pH 8) | 0 |

Preparation of Gel

Reference Example 1-G to Comparative Example 2-G

150 µl of the 8.3Chol-cGltn aqueous solution of Reference Example 1 and 150 µl of the second agent aqueous solution were mixed, put into a mold, and allowed to stand still under a condition of 37° C. for 5 minutes. By this way, a disk gel including 8.3Chol-cGltn and 4S-PEG having a diameter of 4.0 mm and a thickness of 1.0 mm (represented by "Reference Example 1-G", hereinafter represented similarly) was prepared. During the mixing, a predetermined amount of a Brilliant Blue pigment is incorporated in a transparent mixed solution to color the mixed solution so that the size of the gel can be clearly recognized. Subsequently, the respective disk gels shown in Table 2 were prepared in similar manners.

<Measurement of Frequency Wave Number-Dependent Kinetic Elasticity: Measurement of Storage Modulus and Membrane Strength>

Subsequently, using a MCR301 viscoelastic meter, the storage modulus of each disk gel was measured under measurement conditions of an angle frequency wave number area at 0.1 to 100 (1/s) and a distortion of 5%. Furthermore, the storage modulus at an angle frequency wave number of 1.0 (1/s) was deemed as a compressive modulus and indicated in Table 2. FIGS. 4 to 8 each indicate (a) a graph showing the angle frequency wave number-dependency of each disk gel and (b) a bar graph showing the compressive modulus. In either of the graphs, the data of a raw material gelatin (Comparative Example 1-G) and a fibrin sealant (Comparative Example 2-G) are also indicated for comparison.

TABLE 2

| Disk gel | Compressive modulus ((Compressive* modulus (kPa)) |
|---|---|
| Reference Example 1-G | 25 |
| Example 1-G | 29.5 |
| Reference Example 2-G | 18 |
| Reference Example 3-G | 19.5 |
| Reference Example 4-G | 29 |
| Reference Example 5-G | 25 |
| Reference Example 6-G | 24.5 |
| Reference Example 7-G | 19.5 |
| Reference Example 8-G | 23 |
| Reference Example 9-G | 20.5 |
| Example 2-G | 26 |
| Example 3-G | 26.5 |
| Example 4-G | 31 |
| Example 5-G | 30 |
| Example 6-G | 38 |
| Comparative Example 1-G | 21 |
| Comparative Example 2-G | 9 |

*Value of storage modulus at angle frequency wave number 1.0 (1/s)

Figure 4:
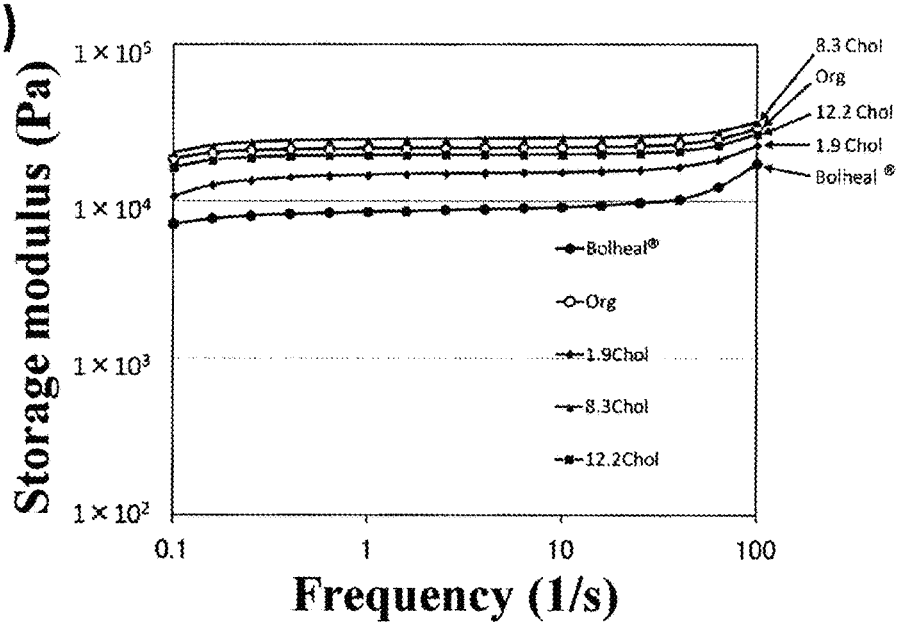
FIG. 4(a) shows a graph showing angle frequency wave number dependency of storage moduluses of disk gels of 1.9Chol-cGltn (Reference Example 2), 8.3Chol-cGltn (Reference Example 1) and 12.2Chol-cGltn (Reference Example 3)
FIG. 4(b) shows a bar graph showing compressive moduluses.
Figure 4:
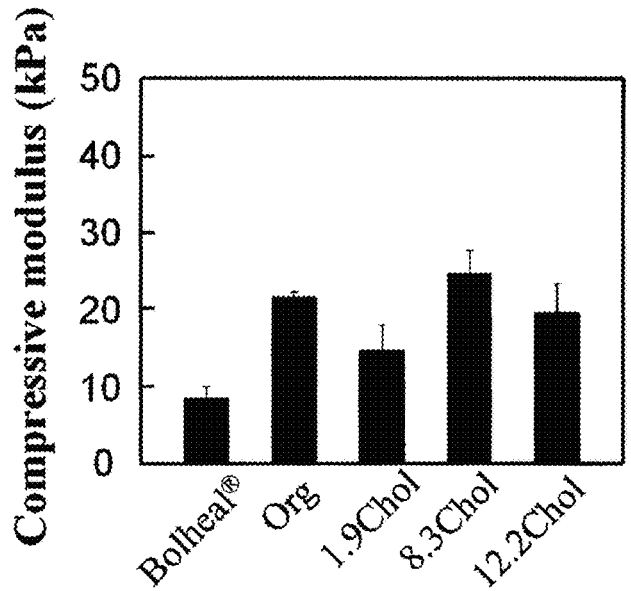
Figure 5A:
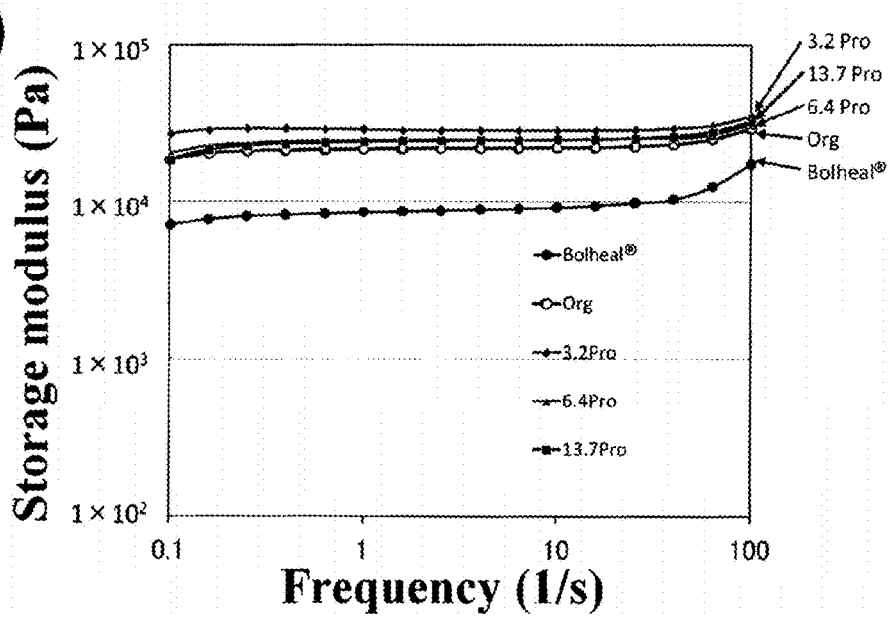
FIG. 5(a) shows a graph showing the angle frequency wave number dependency of the storage moduluses of the disk gels of 3.2Pro-cGltn (Reference Example 4), 6.4Pro-cGltn (Reference Example 5) and 13.7Pro-cGltn (Reference Example 6)
Figure 5B:
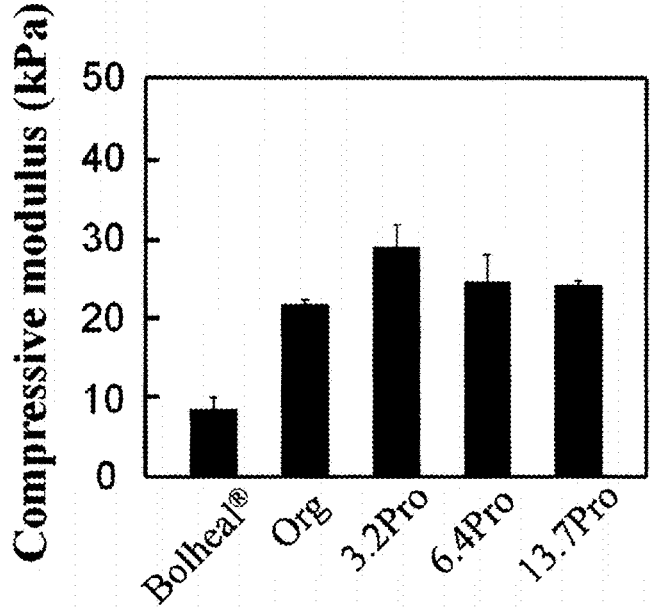
FIG. 5(b) shows a bar graph showing the compressive moduluses.
Figure 6A:
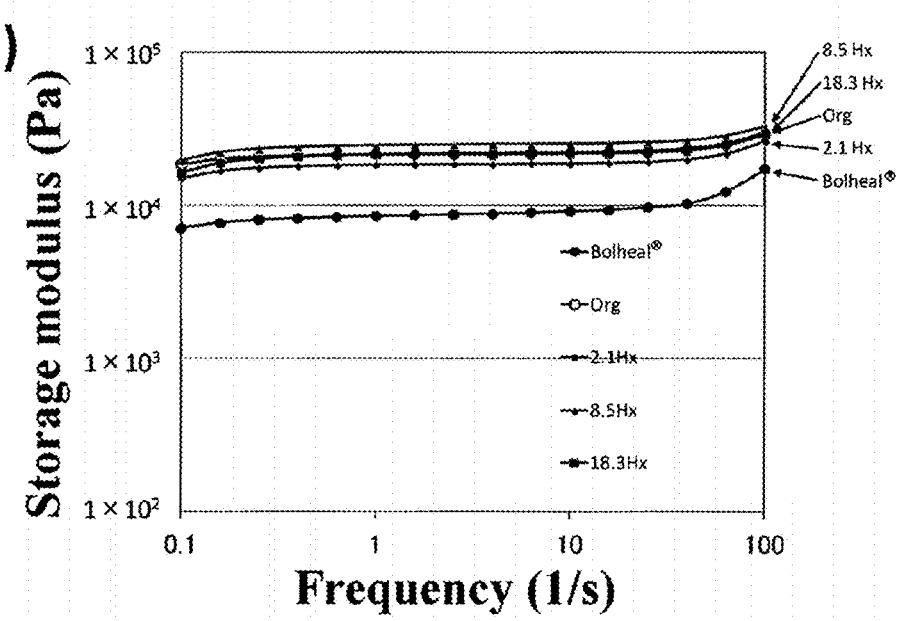
FIG. 6(a) shows a graph showing the angle frequency wave number dependency of the storage moduluses of 2.1Hx-cGltn (Reference Example 7), 8.5Hx-cGltn (Reference Example 8) and 18.3Hx-cGltn (Reference Example 9)
Figure 6B:
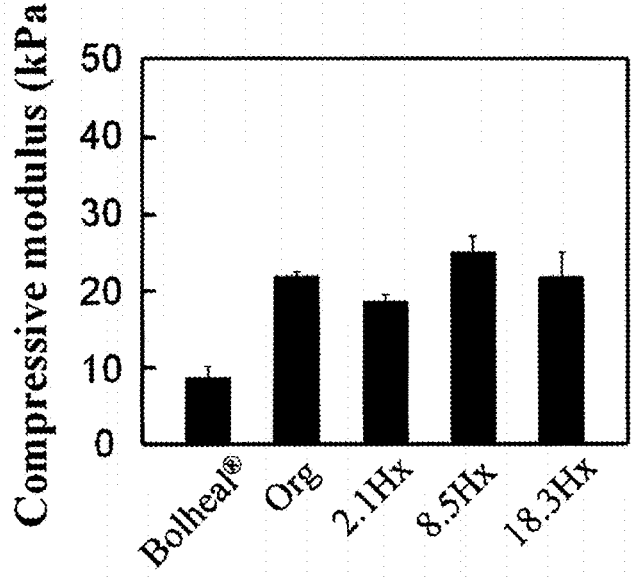
FIG. 6(b) shows a bar graph showing the compressive moduluses.
Figure 8:
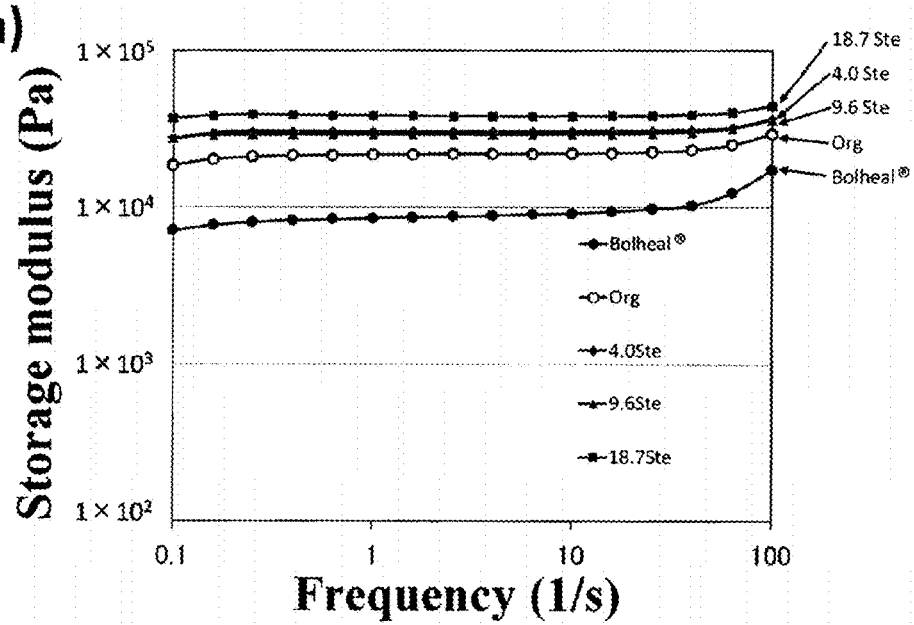
FIG. 8(a) shows a graph showing the angle frequency wave number dependency of the storage moduluses of 4.0Ste-cGltn (Example 5), 9.6Ste-cGltn (Example 1) and 18.7Ste-cGltn (Example 6)
FIG. 8(b) shows a bar graph showing the compressive moduluses.
Figure 8:
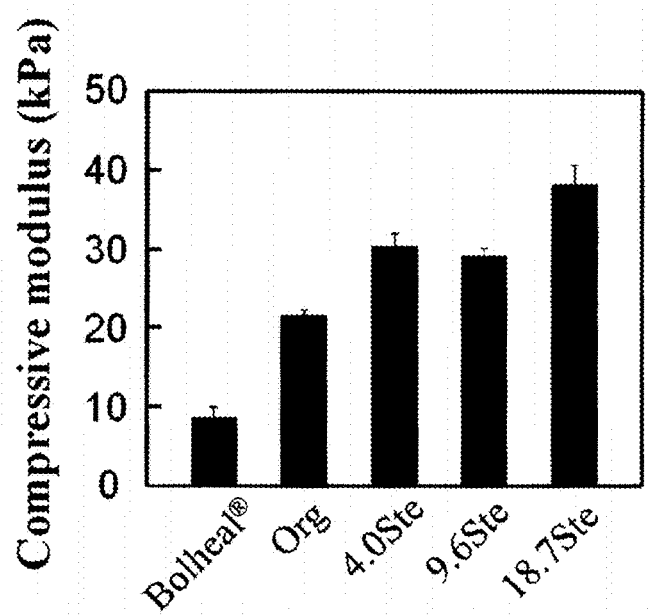

As shown in FIGS. 4 (a) to 8 (a), in the measured frequency wave number area, either of the materials showed a stable storage modulus behavior. Furthermore, either of the disk gels of Reference Examples and Examples had a higher storage modulus than that of the fibrin sealant (Comparative Example 2-G). Among these, Examples 2 to 4 (FIG. 7 (a)) and Examples 1, 5 and 6 (FIG. 8(a)) had a higher storage modulus as compared to that of Comparative Example 1-G.

Figure 9:
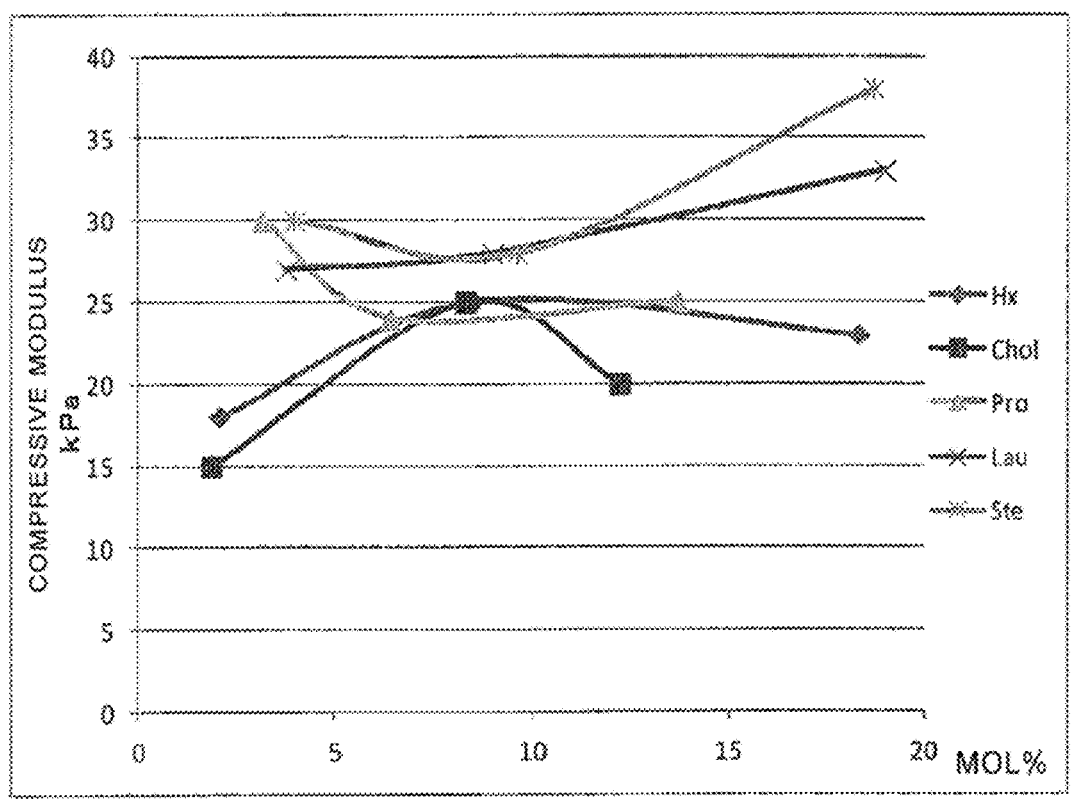
FIG. 9 is a graph in which the compressive moduluses with respect to the substitution rates of the respective hydrophobic groups are plotted.

As shown in FIGS. 4 (b) to 8 (b), it was found that either of the disk gels of Reference Examples and Examples had a higher compressive modulus as compared to that of the fibrin sealant (Comparative Example 2-G), and that, specifically, Examples 1 to 6 (FIGS. 7 (b) and 8 (b)) had higher compressive moduluses than that of the raw material gelatin. FIG. 9 is a drawing showing the relationship between the substitution rate and the compressive modulus for every substituent. As is understood from this drawing, it was found that the hydrophobic groups having 12 carbon atoms (Lau) and 18 carbon atoms (Ste) had high compressive moduluses in a broad range at a substitution rate of from 4 mol % to about 19 mol %, and thus an excellent sealing strength can be achieved when the adhesion strengths of gelatins having these substituents are considered in combination.

Measurement of Gelation Time

Reference Example 1-T

150 μl of the first agent aqueous solution of Reference Example 1, which is an aqueous solution of 8.3Chol-cGltn, and 150 μl of the second agent aqueous solution were mixed and put into a glass tube having a diameter of 16 mm. Subsequently, a magnet was put into the glass tube, and stirring was carried out by using a magnet stirrer under conditions of 37° C. and 280 rpm, and gelation progressed gradually, and the rotation of the magnet became slow. The time until the magnet finally stopped was deemed as a gelation time. Similar measurements were conducted on Reference Example 5, Reference Example 8, Example 3, Example 5 and Comparative Example 1. The results are shown in Table 3.

TABLE 3

|  | Comparative Example 1-T | Reference Example 5-T | Reference Example 8-T | Example 3-T | Example 5-T | Reference Example 1-T |
|---|---|---|---|---|---|---|
| Abbreviation | Org | 6.4 Pro | 8.5 Hx | 9.0 Lau | 9.6 Ste | 8.3 Chol |
| Gelation time (sec) | 39.4 ± 2.9 | 30.8 ± 2.1 | 30.3 ± 2.0 | 30.8 ± 2.7 | 25.3 ± 1.6 | 25.4 ± 2.0 |

Comparative Example 1-T Reference Example 5-T Reference Example 8-T Example 3-T Example 5-T Reference Example 1-T As shown in Table 3, all of the gelatins substituted with hydrophobic groups had shorter gelation times than that of a gelatin free from hydrophobic groups (Org).

Preparation of Sample for Measuring Pressure Resistance Strength

Example 1-R

An air leak model of a lung extracted from a rat was prepared with referring to the method described in Non-patent Literature 5. Since an inflated state and a deflated state are significantly different in a rat lung, an air introduction tube was firstly connected to the throat part of a lung extracted from a rat and occluded by a braid, and the lung extracted from a rat was inflated by introducing air into the lung extracted from a rat.

In the state that the lung was inflated, the surface of the lung extracted from a rat was pricked with an injection needle of 20 gauges (20 G needle) to a depth of about 2 mm to form a defect part, whereby a defect model was prepared. Furthermore, the lung extracted from a rat was stabilized for 5 minutes with putting the atmospheric pressure in the lung and the outer atmospheric pressure into an equilibrium state. Subsequently, a silicone ring having a thickness of 0.5 mm, an inner diameter of 7.0 mm and an outer diameter of 20.0 mm was disposed on the surface of the lung extracted from a rat so that the above-mentioned defect part was positioned on the center part of the ring.

Subsequently, the surgical sealant of Example 1 (including an aqueous solution of 9.6Ste-cGltn and a 4S-PEG aqueous solution) was applied in a circular shape on the surface of the lung in the silicone ring and cured for 5 minutes to seal the defect part, and the silicone ring was removed to give a sample for measuring pressure resistance strength (Example 1-R).

<Measurement of Pressure Resistance Strength>

The obtained sample for measuring pressure resistance strength was immersed in 37° C. saline, and air was sent to the lung at 1 mL/sec. Cracks generated in the sealant, and the air pressure at which generation of bubbles in water was seen (air leak pressure) was deemed as a pressure resistance strength. In similar manners, the pressure resistance strengths were measured for Reference Example 1 (8.3Chol-cGltn) and Comparative Examples 1 and 2. The results are shown in Table 4.

TABLE 4

|  | Air leak pressure (cm H$_2$O) |
|---|---|
| Org | 25.3 ± 2.4 |
| 9.6 Ste | 41.4 ± 4.5 |
| 8.3 Chol | 40.6 ± 8.0 |
| Fibrin | 19.2 ± 0.9 |

As is understood from the above-mentioned table, Example 1 (9.6Ste-cGltn) had a higher pressure resistance strength and a more excellent sealing strength than those of either of Reference Example 1 (8.3Chol-cGltn), Comparative Example 1 (Org) and Comparative Example 2 (fibrin).

<Calculation of Water Content of Immersed Disk Gel>

The respective disk gels of Reference Example 1-G (8.3Chol-cGltn), Example 1-G (9.6Ste-cGltn) and Comparative Example 1-G (Org-cGltn) were made by the above-mentioned method, and immediately immersed in saline at 37° C. At the times when 1, 3, 5, 10, 15, 30, 60, 120 and 240 minutes had passed from the time of the disclosure of the immersion, the mass of the disk gel (mass after immersion for predetermined time: Wt) was measured. After the measurement, in order to remove the sodium ion inside of the gel, the disk gel was immersed in 2 ml of Milli Q water at 37° C. for 24 hours and lyophilized for 48 hours, and the mass of the disk gel (mass after drying: Wd) was measured.

The content % of the water contained in the gel (water content) was calculated from the values of the obtained Wt and Wd by the formula (1). The results are shown in Table 5.

$$\text{Water content}=(Wt-Wd)\times 100 \quad (1)$$

TABLE 5

| Disk gel | Water contents | | |
| | Immediately after preparation (%) | After 60 minutes (%) | After 240 minutes (%) |
|---|---|---|---|
| Reference Example 1-G | 80.23 ± 0.09 | 89.55 ± 0.46 | 89.73 ± 0.15 |
| Example 1-G | 80.17 ± 0.5 | 89.12 ± 0.4 | 89.3 ± 0.34 |
| Comparative Example 1-G | 78.71 ± 0.18 | 89.68 ± 0.4 | 89.97 ± 0.1 |

Figure 10:
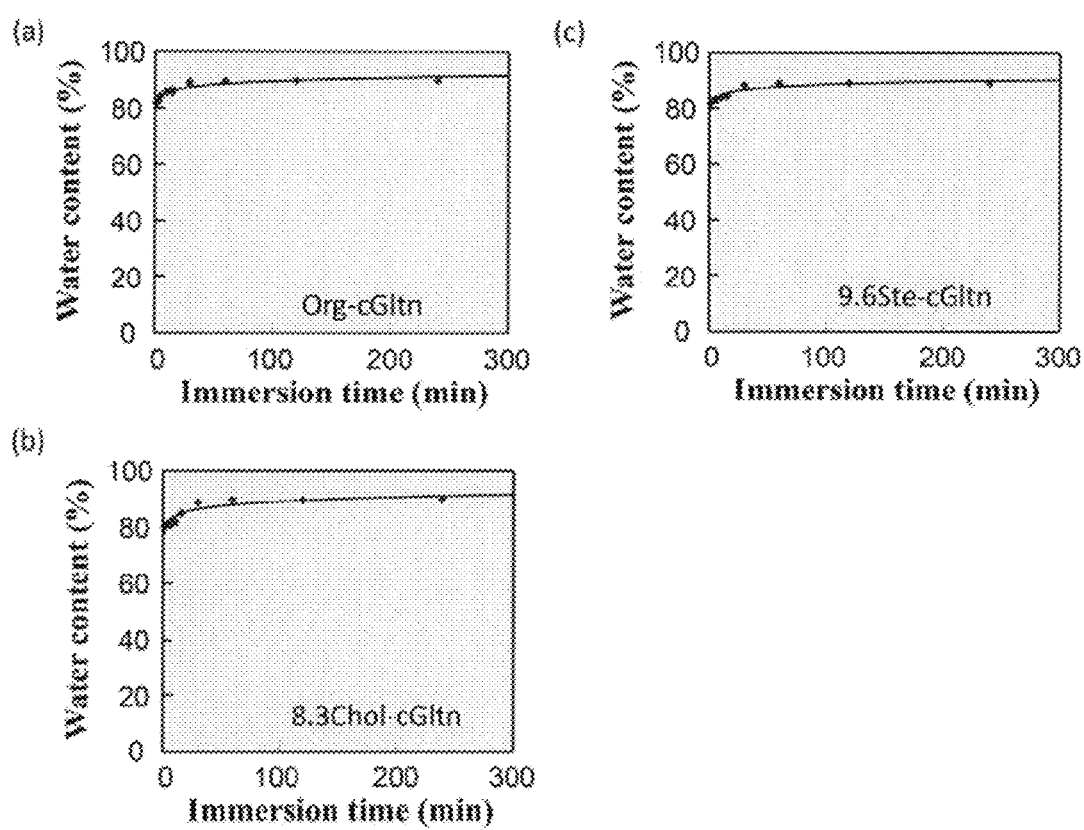
FIG. 10 is a graph showing the change of the water contents (calculated values) of the respective disk gels over time, in which (a) shows Org-cGltn (Comparative Example 1), (b) shows 8.3Chol-cGltn (Reference Example 1), and (c) shows 9.6Ste-cGltn (Example 1).

FIG. 10 is a graph showing the change in the water content (calculated value) of each disk gel over time, wherein (a) represents Org-cGltn (Comparative Example 1-G), (b) represents 8.3Chol-cGltn (Reference Example 1-G), and (c) represents 9.6Ste-cGltn (Example 1-G).

From FIG. 10, in either of the disk gels, the initial water content of about 80% had changed to about 90% at after 30 minutes, and thus reached an approximately equilibrium state. It was confirmed that, when the disk gel immediately after the preparation was immersed, the water content changed, but the change was not significant.

<Change in Swelling in Immersed Disk Gel>

Figure 11:
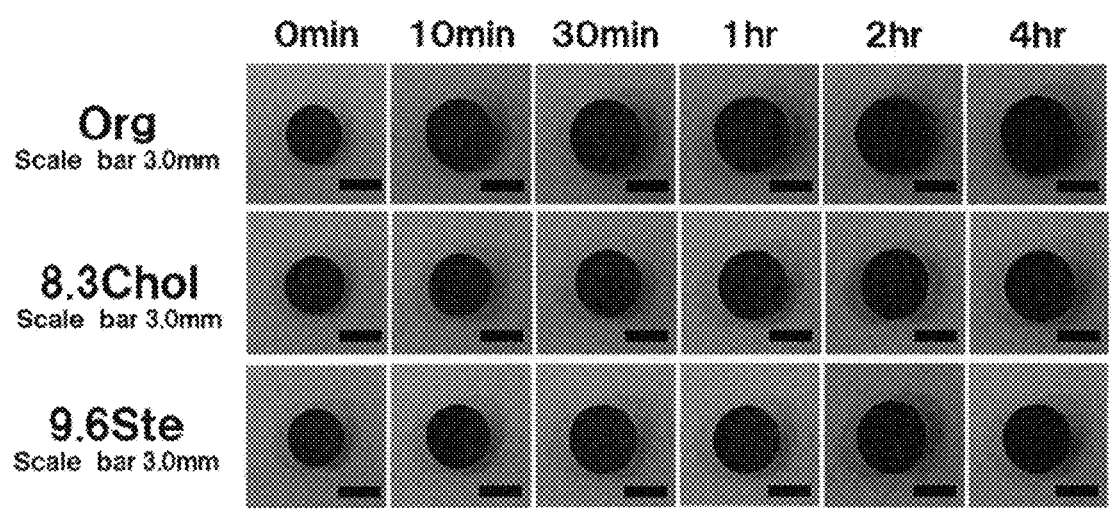
FIG. 11 shows photographs showing the changes over time of the degrees of swelling of the respective disk gels.

In the above-mentioned experiment, the changes in swelling of the respective gels at after 0, 10, 30, 60, 120 and 240 minutes had passed from the initiation of immersion were photographed. FIG. 11 shows photographs showing the changes in swelling of the respective disk gels. As shown in FIG. 11, in the size of the disk gel of Org-cGltn (Comparative Example 1-G), the diameter slightly increased at the time of 10 minutes after the immersion. Thereafter, any significant change was not observed. Furthermore, in the disk gels of 8.3Chol-cGltn (Reference Example 1-G) and 9.6Ste-cGltn (Example 1-G), the diameter slightly increased at after 30 minutes. Thereafter, any significant change was not observed. This is considered to be due to the effect of the hydrophobic groups.

It should be noted that, generally, when a gel swells, the polymer density inside of the gel decreases, and thus it is possible that the membrane strength decreases and gel breaking and peeling from a tissue are caused. Since a surgical sealant is used under a wet environment, the surgical sealant is required to be difficult to swell when used under said environment. In the disk gels of 8.3Chol-cGltn (Reference Example 1-G) and 9.6Ste-cGltn (Example 1-G), the change in swelling was small after 30 minutes after the immersion. It was found from these results that the surgical sealant of the present invention has a sufficient sealing strength for a long period even in a wet environment in the body.

INDUSTRIAL APPLICABILITY

The surgical sealant of the present invention indicates a high sealing strength, and thus is very useful for anastomosis operations of blood vessels and the like.

The invention claimed is:

1. A surgical sealant comprising:
a first agent containing a hydrophobically-modified gelatin derived from a cold-water fish,
a second agent containing a water-soluble molecule for crosslinking, and
a blue colorant,
wherein the water-soluble molecule for crosslinking is at least one selected from the group consisting of polyethylene glycol disuccinimidyl succinate, pentaerythritol-poly(ethylene glycol) ether tetrasuccinimidyl glutarate and poly-L-glutamic acid succinimide,
the hydrophobically-modified gelatin derived from the cold-water fish is a gelatin in which at least a part of amino groups of side chains of the gelatin derived from the cold-water fish has been substituted by hydrophobic groups, and
the hydrophobic groups have a substitution rate of from 3.8 mol % to 19.0 mol % of a lauroyl group or a substitution rate of from 4.0 mol % to 18.7 mol % of a stearoyl group, wherein the substitution rate is calculated based on the following formula:

substitution rate=(number of moles of hydrophobic groups/(total number of moles of hydrophobic groups and reactive amino groups in the gelatin)×100).

2. The surgical sealant according to claim 1, wherein the hydrophobically-modified gelatin derived from the cold-water fish has a molecular weight of 10,000 or more and below 100,000.

3. The surgical sealant according to claim 1, wherein the gelatin derived from the cold-water fish is one or more gelatins derived from the group consisting of red snapper, Alaska Pollack, salmon, and genetically-engineered cold-water fishes thereof.

4. The surgical sealant according to claim 1, wherein the gelatin derived from the cold-water fish contains 190 or less imino acids per 1,000 constitutional amino acids.

5. The surgical sealant according to claim 1, wherein the hydrophobic groups are linked to a part of the amino groups of Lys that is one of the constitutional amino acids of the gelatin derived from the cold-water fish.

6. The surgical sealant according to claim 1, wherein the water-soluble molecule for crosslinking is pentaerythritol-poly(ethylene glycol) ether tetrasuccinimidyl glutarate.

* * * * *